(12) United States Patent
Peikon et al.

(10) Patent No.: US 10,017,758 B1
(45) Date of Patent: Jul. 10, 2018

(54) PROTEIN-PROTEIN INTERACTION GUIDED MATING OF YEAST

(71) Applicant: Verily Life Sciences LLC, Mountain View, CA (US)

(72) Inventors: Ian Peikon, Bethpage, NY (US); Gary Tong, Berkeley, CA (US)

(73) Assignee: VERILY LIFE SCIENCES LLC, Sout San Francisco, CA (US)

( * ) Notice: Subject to any disclaimer, the term of this patent is extended or adjusted under 35 U.S.C. 154(b) by 0 days.

(21) Appl. No.: 15/605,183

(22) Filed: May 25, 2017

(51) Int. Cl.
*G01N 33/68* (2006.01)
*C12N 15/10* (2006.01)

(52) U.S. Cl.
CPC ..... *C12N 15/1055* (2013.01); *C12N 15/1037* (2013.01); *G01N 33/6845* (2013.01)

(58) Field of Classification Search
None
See application file for complete search history.

(56) References Cited

U.S. PATENT DOCUMENTS

| | | | | |
|---|---|---|---|---|
| 2005/0158708 | A1* | 7/2005 | Alroy | C07D 207/416 435/5 |
| 2014/0120625 | A1* | 5/2014 | Udagawa | C12N 15/80 435/478 |
| 2017/0205421 | A1* | 7/2017 | Baker | G01N 33/6845 |

OTHER PUBLICATIONS

Gietz et al., "Transformation of yeast by lithium acetate/single-stranded carrier DNA/polyethylene glycol method", Methods in enzymology 350 (2002): 87-96.

Hafner et al., "Barcoded cDNA library preparation for small RNA profiling by next-generation sequencing", Methods 58.2 (2012): 164-170.

* cited by examiner

*Primary Examiner* — James S Ketter

(74) *Attorney, Agent, or Firm* — Kilpatrick Townsend & Stockton LLP

(57) ABSTRACT

The invention relates to methods and compositions useful for detection of protein-protein interactions between cell surface proteins.

32 Claims, 2 Drawing Sheets

PROTEIN-PROTEIN INTERACTION GUIDED MATING OF YEAST

PRIOR RELATED APPLICATION

This application claims priority to U.S. Provisional Application No. 62/341,302, filed May 25, 2016, which is hereby incorporated by reference in its entirety herein.

FIELD

Embodiments of the present disclosure relate to detecting protein-protein interactions between cell surface proteins. In particular, compositions and methods are provided for detecting protein-protein interactions between cell surface proteins on yeast cells.

BACKGROUND

Protein-protein interactions can be assayed at high throughput using methods such as yeast two-hybrid screening. However, these methods are generally not well adapted to the study of cell surface proteins, as these methods require laborious analysis of assay results and can yield high false-positive result rates. Therefore, compositions and methods for reliably identifying protein-protein interactions between cell surface proteins are necessary.

SUMMARY

Provided herein are methods for detecting a protein-protein interaction between cell surface proteins. These methods may include providing a first plurality of haploid yeast cells of a first mating type, the first plurality of cells comprising a library of first plasmids, wherein each plasmid in the library comprises: a first selectable marker, a unique molecular barcode sequence operatively linked to a first recombination site, and a sequence encoding a unique cell surface protein, such that each unique molecular barcode is associated with a unique cell surface protein. The methods may also include providing a second plurality of haploid yeast cells of a second mating type, the second plurality of cells comprising a library of second plasmids, wherein each plasmid in the library comprises: a second selectable marker, a unique oligonucleotide molecular barcode sequence operatively linked to a second recombination site, and a sequence encoding a unique cell surface protein, such that each unique molecular barcode is associated with a unique cell surface protein, wherein the unique cell surface proteins of the library of first plasmids and the unique cell surface proteins of the library of second plasmids comprise potential binding pairs. These methods may also include contacting the first plurality of haploid yeast cells with the second plurality of haploid yeast cells under conditions where a specific binding interaction between a cell surface protein of the library of first plasmids and a cell surface protein of the library of second plasmids promotes mating of the first and second plurality of haploid yeast cells to produce diploid yeast cells. Also, the methods may also include recombining within the diploid cells portions of the plasmids to generate a recombined molecular barcode sequence comprising at least a portion of the unique barcode associated with one of the unique cell surface proteins of the library of first plasmids and a portion of the unique molecular barcode associated with one of the unique cell surface proteins of the library of second plasmids. The method may also include sequencing at least a portion of the recombined molecular barcode sequence from the diploid cells to identify a surface protein from the library of first plasmids and a cell surface protein from the library of second plasmids that interact, thus detecting a protein-protein interaction between the cell surface proteins.

In some embodiments, the first selectable marker and the second selectable marker are the same. In other embodiments, the first selectable marker and the second selectable marker are different. In some embodiments, the methods may also include the step of using at least one of the selectable markers to select for diploid cells that contain at least one each of the first and second plasmids after contacting the first plurality of haploid yeast cells with the second plurality of haploid yeast cells. In some embodiments, the recombined molecular barcode sequence from two or more diploid cells are sequenced to detect two or more different cell surface protein-protein interactions.

In some embodiments, the specific binding interaction between cell surface proteins of the library of first plasmids and the cell surface protein of the library of second plasmids occurs in a dilute yeast cell mixture. In certain embodiments, the dilute mixture has a spectral absorbance of less than 2.0 $O.D._{600\ nm}$. In some embodiments, the binding affinity between the first cell surface protein and the second cell surface protein is greater than the mating strain binding affinity between a yeast cell from the first mating strain and a yeast cell from the second mating strain. In certain embodiments, the binding affinity is at least two-fold, five-fold or ten-fold greater than the mating strain affinity.

In some embodiments, recombination is site-specific. In certain embodiments, the recombination is CRE-Lox recombination or FLP-FRT recombination. In some embodiments, recombination is unidirectional. Exemplary embodiments of unidirectional integration is unidirectional integration performed by serine integrase or PhiC31integrase. In some embodiments, the plasmids recombine with the genome of the haploid yeast cell or the diploid yeast cell.

In some embodiments, the cell surface protein is a transmembrane protein, an integral membrane protein or a peripheral membrane protein. In other embodiments, the cell surface protein is transiently associated with the membrane. In yet other embodiments, the cell surface protein is a hybrid protein comprising at least a portion of a native, soluble protein not associated with the membrane fused to at least a portion of a native cell surface protein, wherein the at least a portion of the native, soluble protein is expressed on the outer surface of the yeast haploid cell. In certain embodiments, a linker connects the at least a portion of the native, soluble protein to the at least a portion of the native cell surface protein in the hybrid protein expressed in the haploid yeast cell. In some embodiments, the cell surface protein is encoded by a mammalian gene. In other embodiments, the cell surface protein is encoded by a human gene. In yet other embodiments, the cell surface protein is encoded by a gene found in a non-yeast organism.

In some embodiments, at least one of the haploid yeast cells has a gene coding for a yeast mating factor that is controlled by an inducible promoter.

In some embodiments, mating of the haploid yeast cells is induced by activating the inducible promoter controlling expression of mating factor. In other embodiments, the haploid yeast cells are placed in conditions where the haploid cells will not mate unless the cell surface proteins interact.

In some embodiments, the unique oligonucleotide molecular barcode sequence is between 5 and 50 nucleotides in length. In other embodiments, the unique molecular identifier sequence is between 5 and 25 nucleotides in length.

In some embodiments, sequencing comprises amplification of the recombined molecular bar code sequence. In other embodiments, sequencing comprises amplification of at least a portion of the sequence that encodes the cell surface protein.

In addition, provided herein are compositions to detect a protein-protein interaction between cell surface proteins. Provided herein is a population of haploid yeast cells, wherein the yeast cells contain a genetic element comprising a sequence coding for a selectable marker, a sequence coding for a cell surface protein and a unique molecular barcode sequence. In some embodiments, the cell surface protein is mammalian. In some embodiments, the cell surface protein is human.

Also provided is a composition comprising a first plurality of haploid yeast cells of a first mating type, the first plurality of cells comprising a library of first plasmids, wherein each plasmid in the library comprises a first selectable marker, a unique molecular barcode sequence operatively linked to a first recombination site, and a sequence encoding a unique cell surface protein, such that each unique molecular barcode is associated with a unique cell surface protein. The composition may further comprise a second plurality of haploid yeast cells of a second mating type, the second plurality of cells comprising a library of second plasmids, wherein each plasmid in the library comprises a second selectable marker, a unique oligonucleotide molecular barcode sequence operatively linked to a second recombination site, and a sequence encoding a unique cell surface protein, such that each unique molecular barcode is associated with a unique cell surface protein, wherein the unique cell surface proteins of the library of first plasmids and the unique cell surface proteins of the library of second plasmids comprise potential specific binding pairs.

Also provided is a kit for the detection of protein-protein interactions between cell surface proteins that comprises a plurality of plasmids, wherein each plasmid comprises: a selectable marker, a unique oligonucleotide molecular barcode sequence operatively linked to a recombination site, and a sequence encoding a cell surface protein, wherein each unique molecular barcode is associated with a unique cell surface protein. The kit may also comprise instructions for use.

Each of the compositions and kits, may comprise any of the embodiments described herein for the methods. For example, for the compositions and kits, the first selectable marker and the second selectable marker may be the same or different, and may be used to select for diploid cells that contain at least one each of the first and second plasmids. In some embodiments, the bar codes may recombine to detect two or more different cell surface protein-protein interactions.

In some embodiments, the cell surface protein is a transmembrane protein, an integral membrane protein or a peripheral membrane protein. In other embodiments, the cell surface protein is transiently associated with the membrane. In yet other embodiments, the cell surface protein is a hybrid protein comprising at least a portion of a native, soluble protein not associated with the membrane fused to at least a portion of a native cell surface protein, wherein the at least a portion of the native, soluble protein is expressed on the outer surface of the yeast haploid cell. In certain embodiments, a linker connects the at least a portion of the native, soluble protein to the at least a portion of the native cell surface protein in the hybrid protein expressed in the haploid yeast cell. In some embodiments, the cell surface protein is encoded by a mammalian gene. In other embodiments, the cell surface protein is encoded by a human gene. In yet other embodiments, the cell surface protein is encoded by a gene found in a non-yeast organism.

In some embodiments, at least one of the haploid yeast cells has a gene coding for a yeast mating factor that is controlled by an inducible promoter.

In some embodiments, mating of the haploid yeast cells is induced by activating the inducible promoter controlling expression of mating factor. In other embodiments, the haploid yeast cells are placed in conditions where the haploid cells will not mate unless the cell surface proteins interact.

In some embodiments, the unique oligonucleotide molecular barcode sequence is between 5 and 50 nucleotides in length. In other embodiments, the unique molecular identifier sequence is between 5 and 25 nucleotides in length.

Other aspects of the disclosure are provided in more detail herein.

DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

DESCRIPTION

Figure 1:
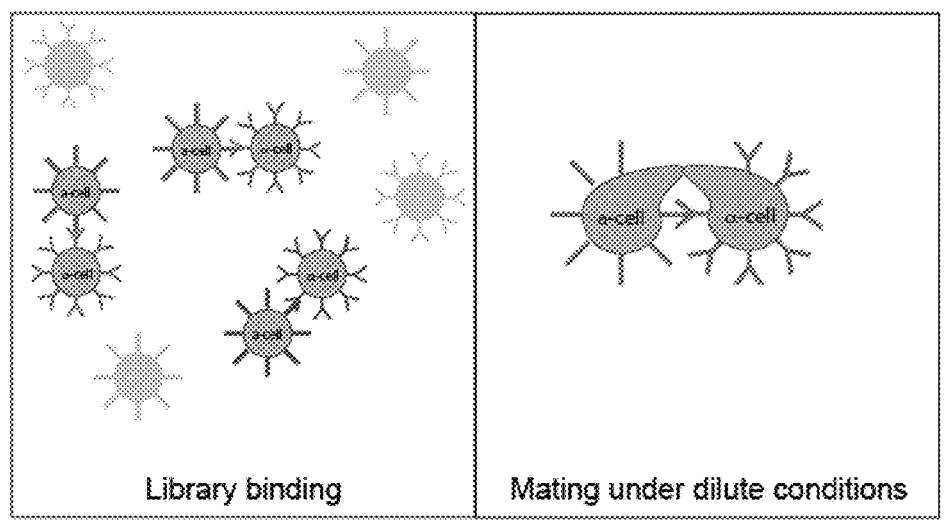
FIG. 1 is a schematic showing guided mating of haploid yeast cells by interaction of cell surface proteins between yeast cells of opposite mating type, under dilute yeast cell conditions. Mating is induced by inducing the expression of the a-factor and the α-factor which allows the formation of diploid cells containing the genetic information for both of the protein-protein interaction partners. The left panel depicts a mixture of a plurality of haploid yeast cells of A-mating type and α-mating type expressing a plurality of cell surface proteins, wherein the cells express distinct or unique cell surface proteins. The right panel depicts interaction between two haploid yeast cells of opposite mating type under dilute yeast cell concentrations where cell surface proteins between the two interacting haploid yeast cells promote mating which otherwise would not occur, and the cells have formed a shmoo structure for mating.

The following description recites various aspects and embodiments of the present compositions and methods. No particular embodiment is intended to define the scope of the compositions and methods. Rather, the embodiments merely provide non-limiting examples various methods and systems that are at least included within the scope of the disclosed compositions and methods. The description is to be read from the perspective of one of ordinary skill in the art; therefore, information well known to the skilled artisan is not necessarily included.

Briefly, and as described in more detail below, described herein are methods and compositions for the detection of cell surface protein-protein interactions. Yeast have long served as a useful model and system to study the function of genes isolated from other organisms (heterologous genes) since yeast can be efficiently transformed by nucleic acid molecules, for example, circular or linear plasmids carrying foreign genes under the control of a yeast transcription promoter to yield cDNA libraries. Protein-protein interactions can be assayed at high throughput using methods such as yeast two-hybrid screening. However, there are limitations to these methods, since they are not generally amenable to the study of membrane proteins.

Provided herein are methods and compositions useful for identification of cell surface proteins such as receptors and their ligands. There are many examples of membrane protein interactions that can be identified, for example, interactions between T-cells and their cognate MHC-antigen pairs, interactions between cytokines and their receptors, interactions between growth factors and their receptors, or interactions between extracellular matrix proteins and their receptors, to name a few. The methods and compositions provided herein can also be used to identify membrane proteins and soluble ligands. The soluble ligands can be expressed on the surface of the haploid yeast cell by cloning the coding sequence for the soluble ligand into the coding sequence of the extracellular domain of a membrane protein. The invention allows for two libraries coding for cell surface proteins wherein each library is expressed in each mating type of haploid yeast cell. Alternatively, single libraries coding for cell surface proteins can be expressed in one mating type of the haploid yeast cells and used to identify the interacting proteins for a smaller group of proteins of interest that are expressed on the surface of the haploid yeast cells of the opposite mating type.

Methods and compositions useful for detection of protein-protein interactions between cell surface proteins are provided. Disclosed herein are methods and compositions using genetic molecular barcode exchange and sequencing to identify protein-protein interactions between cell surface proteins expressed on haploid yeast cells. When sufficient amount of pheromones are secreted, haploid yeast cells of different mating types (a or α) will mate resulting in a diploid cell. If this is done under conditions where pheromones and yeast cells are diluted, the chance of mating asymptotically approaches zero. However, under the same conditions, if two cells have affinity for one another (i.e., because of a transcellular protein-protein interaction), mating can be directed to occur only between those cells to produce diploid cells. Afterwards, coding sequences of the individual proteins or barcode sequences corresponding to the individual proteins in the resultant diploid cell can be joined by a variety of recombination techniques and sequenced to identify the individual proteins involved in cell surface protein-protein interactions.

Definitions

Terms used in the claims and specification are defined as set forth below unless otherwise specified.

The term "cell surface protein" refers to any protein that includes at least a portion that is located on the extracellular surface of the cell, including proteins that are not physically associated to the plasma membrane, proteins that are displayed on the plasma membrane artificially through cloning techniques, proteins that are associated either directly or indirectly with other membrane-associated proteins, proteins that are either transiently or stably located on the outer surface of the cell, transmembrane proteins, integral membrane proteins and peripheral membrane proteins. The term "cell surface protein" also refers to a fragment of a protein (i.e., polypeptide) located on the extracellular surface of the cell or a fragment of a protein that is not normally located on the extracellular surface of the cell, as long as the fragment is expressed on the cell surface of the yeast cells used in the compositions and methods provided herein.

The term "guided mating of haploid yeast cells" refers to placing haploid yeast cells under conditions where yeast cell mating is promoted, at least in part, by trans-cellular protein-protein interactions to induce shmoo formation of the haploid yeast cells. The conditions allowing for guided mating of haploid yeast cells may include dilution of the yeast cells and/or the presence of a mating factor. Expression of a mating factor by haploid yeast cells in guided mating of haploid yeast cells can be induced using a regulatable, inducible promoter to promote mating of haploid yeast cells expressing cell surface proteins that undergo trans-cellular protein-protein interactions. The inducible promoter can be any artificially controlled promoter modulated by a chemical compound or an abiotic factor. The chemical compound controlling the promoter can be, but is not limited to, an antibiotic, a metal or transition metal such as copper, an alcohol, steroid or herbicide. The abiotic factor controlling the promoter can be, but is not limited to, light, oxygen, heat, cold or wounding. The inducible promoter can also be a synthetic promoter that is designed from more than one primary promoter element from diverse origins. In exemplary embodiments, the inducible promoter is a Tetracycline-inducible promoter, Gal1, Met25 or CUP1. Other exemplary inducible promoters include but are not limited to, alcohol-regulated promoters, metal-regulated promoters and steroid-regulated promoters.

The term "unique oligonucleotide molecular barcode sequence" refers to a sequence that can be used to identify the specific oligonucleotide through polymerase chain reaction and sequencing methods. In the methods and compositions provided herein, each unique barcode sequence can be associated with a unique cell surface protein. In other words, each cell surface protein can be associated with a different molecule barcode such that a single, unique barcode is associated with each protein being expressed on the cell surface of a yeast cell.

The term "sequencing" refers to all methods related to sequencing nucleic acid, including, high throughput sequencing. Sequencing methods include, but are not limited to, shotgun sequencing, bridge PCR, Sanger sequencing (including microfluidic Sanger sequencing), pyrosequencing, massively parallel signature sequencing, nanopore DNA sequencing, single molecule real-time sequencing (SMRT) (Pacific Biosciences, Menlo Park, Calif.), ion semiconductor sequencing, ligation sequencing, sequencing by synthesis (Illumina, San Diego, Ca), Polony sequencing, next generation sequencing, 454 sequencing, solid phase sequencing, DNA nanoball sequencing, heliscope single molecule sequencing, mass spectroscopy sequencing, pyrosequencing, Supported Oligo Ligation Detection (SOLiD) sequencing, DNA microarray sequencing, RNAP sequencing, tunneling currents DNA sequencing, and any other DNA sequencing method identified in the future. One or more of the sequencing methods described herein may be used in high throughput sequencing methods.

The term "plasmid" refers to a circular, double-stranded DNA containing sequences of interest, for example, a sequence encoding a cell surface protein. In some embodiments, a plasmid can further comprises regulatory sequences or genetic elements that are operatively linked to a sequence encoding of a cell surface protein. In some embodiments, the plasmid comprises sequences that are complementary to oligonucleotide primers used to amplify a sequence or barcode of interest.

The term "plasmid library" refers to a population of double stranded DNA circular plasmids comprising more than one sequence encoding a protein of interest, for example, a cell surface protein. The plasmid libraries can comprise sequences derived from complementary DNA (cDNA), sequences generated from mRNA (cDNA library), or genomic DNA sequences. These sequences can be inserted into one or more plasmids using conventional cloning methods. The sequences encoding a protein of interest can be operationally linked to a promoter sequence to direct the expression of the protein of interest encoded by the sequence.

The term "selectable marker" refers to a gene that encodes a protein that allows the cell expressing the gene to be identified and/or isolated from other cells in the population. Selectable markers include, but are not limited to, genes that encode drug resistance, fluorescence, essential genes for growth in limiting conditions, etc.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term "sufficient amount" means an amount sufficient to produce a desired effect.

It must be noted that, as used in the specification and the appended claims, the singular forms "a," "an" and "the" include plural referents unless the context clearly dictates otherwise. It is also understood that, as used in the specification and the appended claims, "or" includes "and/or," unless the context clearly dictates otherwise.

Methods

Provided herein are methods for detecting a protein-protein interaction between cell surface proteins. These methods may include providing a first plurality of haploid yeast cells of a first mating type, the first plurality of cells comprising a library of first plasmids, wherein each plasmid in the library comprises: a first selectable marker, a unique molecular barcode sequence operatively linked to a first recombination site, and a sequence encoding a unique cell surface protein, such that each unique molecular barcode is associated with a unique cell surface protein. The method may also include providing a second plurality of haploid yeast cells of a second mating type, the second plurality of cells comprising a library of second plasmids, wherein each plasmid in the library comprises: a second selectable marker, a unique oligonucleotide molecular barcode sequence operatively linked to a second recombination site, and a sequence encoding a unique cell surface protein, such that each unique molecular barcode is associated with a unique cell surface protein, wherein the unique cell surface proteins of the library of first plasmids and the unique cell surface proteins of the library of second plasmids comprise potential binding pairs. These methods may also include contacting the first plurality of haploid yeast cells with the second plurality of haploid yeast cells under conditions where a specific binding interaction between a cell surface protein of the library of first plasmids and a cell surface protein of the library of second plasmids promotes mating of the first and second plurality of haploid yeast cells to produce diploid yeast cells. These methods may also include recombining within the diploid cells portions of the plasmids to generate a recombined molecular barcode sequence comprising at least a portion of the unique barcode associated with one of the unique cell surface proteins of the library of first plasmids and a portion of the unique molecular barcode associated with one of the unique cell surface proteins of the library of second plasmids. Also, the method may include sequencing at least a portion of the recombined molecular barcode sequence from the diploid cells to identify a surface protein from the library of first plasmids and a cell surface protein from the library of second plasmids that interact, thus detecting a protein-protein interaction between the cell surface proteins.

Yeast Cells and Plasmid Libraries

The methods provided herein can be performed using standard yeast cell preparations, including either *Schizosaccharomyces pombe* or *Saccharomyces cerevisiae*, *S. cerevisiae* is readily available, its genome is well characterized, genetic methodologies are well established and culturing conditions are well known. Unless otherwise stated, commonly used methods for culturing, maintaining, mating and transforming yeast can follow the protocols detailed in Adams, A., D. E. Gottschling, C. A. Kaiser and T. Steams. 1998. Methods in yeast genetics. Cold Spring Harbor Laboratory Press, Cold Spring Harbor.

There are various appropriate media to grow or maintain yeast, and conditions such as the binding affinities, stability or solubility of the proteins to be tested, or the particular dilution of yeast cells used for mating may dictate the type of medium used. Useful growth media include (yeast extract peptone dextrose (YPD, YEPD)) or synthetic defined media. The cultures can be serially maintained at about 30° C.

In certain embodiments, yeast transformations can be performed using lithium chloride (LiCl), lithium acetate, electroporation, biolistic, glass bead methods or any other method commonly known in the art. In other aspects, lithium chloride or lithium acetate are used with or without heat shock.

In some embodiments, the first and second plurality of haploid yeast cells are of opposite mating types. Yeast cells from opposite mating types can be used to make pluralities of yeast cells comprising a library of plasmids. For example, a first plurality of yeast cells comprising a library of first plasmids and a second plurality of yeast cells comprising a library of second plasmids can be constructed, wherein the first plurality of yeast cells and the second plurality of yeast cells are of opposite mating types. For example, a first plurality of a-type haploid yeasts comprising a library of first plasmids can be produced via transformation with a library of plasmids encoding cell surface proteins and optionally carrying a selectable marker. The transformed DNA carries genetic elements that direct the expression of a protein to be expressed on the yeast cell surface, allowing yeast to display specific proteins on the plasma membrane cell surface. A second plurality of a-type yeast cell comprising a library of second plasmids is similarly constructed. In some embodiments, the first library of plasmids encodes cell surface proteins that can interact with cell surface proteins encoded by the second library of plasmids. For example, and not to be limiting, the first library of plasmids can encode cell surface receptors and the second library of plasmids can encode ligands that bind to the cell surface receptors encoded by the first library of plasmids. The plasmid libraries can comprise a plurality of genetic elements, for example, coding sequences and/or regulatory sequences, derived from cells. The cells can be from any species, eukaryotic or prokaryotic organism, including any mammalian cells or human cells. In an embodiment, the library is a cDNA library from human cells. In the methods provided herein, any of the libraries of plasmids can comprise plasmids encoding 5, 10, 20, 30, 40, 50, 60, 70, 80, 90, 100, 200, 300, 400, 500, 600, 700, 800, 900, 1000 or more cell surface proteins or fragments thereof.

The yeast cell libraries can be made by performing transformation and using any suitable markers for selection known in the art. For example, the markers confer resistance to the antibiotics hygromycin B (HYgR), nourseothricin (NatR) and bialaphos (PAT) can be used. Other dominant selectable markers selected from the group consisting of: LEU2, LYS2, URA3, TRP1, HIS3 and ADE2 may be used. Alternatively, the markers NatMX (NAT) and KanMX (KAN) can be used. For example, a plasmid library encoding cell surface receptors is transformed into mating type A haploid yeast cells (yeast library-a) and a plasmid library encoding cognate cell surface ligands (yeast library-α) is transformed into mating type alpha haploid yeast cells. For example, the selectable marker encoded in the plasmids carrying the sequence encoding the receptors can be drug resistance, such as HygR, and the selectable marker encoded in the plasmids carrying the sequence for the cell surface ligand can be KanMX resistance. The yeast cell libraries are each grown and maintained on selective medium, such as medium harboring either HYgR or KanMX.

In an embodiment, two simplified plasmid cDNA libraries can be constructed as a positive control for determining the optimization of mating conditions. These exemplary simplified plasmid cDNA libraries can comprise sequences coding for five single-pass or single transmembrane domain receptors and sequences coding for a cognate cell surface ligand for each receptor. Examples of single-pass receptors comprise but are not limited to, immunoglobulin proteins, Toll-like Receptors, Epidermal growth factor-like receptors and Notch receptors. cDNA sequences derived from human, acute T cell leukemia cell line Jurkat cells encoding cell surface receptor sequences and cognate cell surface ligands, such as Major Histocompatibility Complex proteins or Notch ligands. These can be cloned using standard molecular biology techniques into plasmids linked to a promoter sequence (such as a yeast transcriptional promoter or a viral promoter, such as CMV5) to drive expression of the receptors and cell surface ligands as well as a selectable marker. The plasmid libraries can be used to transform competent yeast cells (e.g., *Saccharomyces cerevisiae*) to create yeast cell libraries comprising the plasmids. For profiling protein-protein interactions, yeast cell libraries are constructed by transforming haploid yeast cells of opposite mating type with cDNA libraries derived from cell lines, primary cells or primary cells which have been cultured for any given time and/or engineered to express recombinant proteins. Examples of cell lines include but are not limited to: mammalian cell lines, such as Jurkat cells, HeLa cells and mouse NIH 3T3 cells.

In other embodiments, cDNA libraries can be constructed using sequencing information obtained from, but not limited to, publically available database sequences or in-house sequencing data. cDNA libraries from exemplary cell lines are also commercially available and may be obtained from commercial entities (such as GeneCopoeia). cDNA sequences can be cloned into library expression vectors harboring selectable markers and loxP recombination sites. In some embodiments, the cDNAs can be cloned into the library vector using conventional cloning techniques or a kit designed for generation of expression libraries, such as In-Fusion® SMARTer® directional cDNA library construction kit (Clonetech). cDNA can be generated from cells of interest using conventional molecular biology techniques. The cells of interest may be insect cells, mammalian, human or cells from any other non-yeast species. The cDNA may be amplified prior to cloning the cDNAs into the library vector. In certain embodiments, particular cDNAs of interest may be amplified by polymerase chain reaction to create cDNA libraries comprising a selected sub-set of the cDNAs from the cells of interest. In certain embodiments the cDNA is not amplified prior to library construction. In certain other embodiments, the cDNA is modified prior to cloning into the vector library. In other embodiments, the molecular barcodes are added to the cDNA sequence prior to cloning into the vector library. In other embodiments, selectable marker sequences are added or cloned adjacent to the cDNA sequence. In yet other embodiments, sequences complementary or identical to primer binding sites to be used for amplification or sequencing of the cDNA sequence are added to the cDNA sequence.

Unique oligonucleotide barcode sequences can be generated for each cDNA sequence using barcoded oligonucleotide adapters during the reverse transcription of mRNAs to generate the barcoded cDNAs that are cloned into the library plasmid (Hafner et al., Methods, 58(2): 164-170 (2013). Alternatively, the unique bar code sequence oligonucleotides can be synthesized using mixed bases and cloned into plasmids separately. The bar code sequences may be 1-5 nucleotides in length, 5-10 nucleotides in length, 10-15 nucleotides in length, 15-20 nucleotides in length, 20-25 nucleotides in length or more than 25 nucleotides in length. Optionally, the barcode sequences can be operatively linked to one or more recombination sites.

Mating

In an embodiment, for both strains of haploid yeast cell libraries, the expression of the a-factor or α-factor is rendered inducible by application of an exogenous chemical (for example, by controlling their expression through the activation of an inducible promoter such as, the Gal1 promoter, tetracycline-regulated promoter, alcohol-regulated promoter, metal-regulated promoter or a steroid-regulated promoter). The yeast of different mating types are grown separately to the end of log phase, before they are mated.

Mating can be performed by mixing of haploid yeast cell library liquid cultures and/or streaking mating mixtures on top of plates with solid medium. In an embodiment, mating is performed by mixing liquid cultures of the haploid yeast cell libraries. Pre-determined volumes of haploid yeast cell library liquid cultures are grown to an optimal optical density or yeast cell concentration and are mixed. Alternatively, serial dilutions of the haploid yeast cell libraries are created to determine the optimal volume and/or concentrations of yeast cells to promote guided mating of the yeast cells induced by the interaction of the heterologous cell surface proteins. Upon mixing, protein-protein interactions will direct the binding of yeast of different mating types. In certain embodiments, mating factor is induced prior to, after or at the time of mixing at a sufficient amount to promote preferential mating of haploid yeast cells that result in protein-protein interaction between the heterologous cell surface proteins. After binding, the yeast cells can be diluted to a limiting dilution once more, limiting further cell-cell interactions from occurring. Various volumes of the yeast libraries-a and -α can be mixed in flasks containing liquid yeast culture medium and incubated at 30° C. with or without shaking. The yeast cells can then be counted and the serial dilution can be performed to create a series of concentrations of yeast library cell mixtures to test for guided mating induced by the interaction of the heterologous cell surface proteins. In certain embodiments, the yeast cell culture concentration at the limiting dilutions can be determined by the spectral absorbance at $O.D._{600\ nm}$. The limiting dilution may have a spectral absorbance of less than 0.0001 $O.D._{600\ nm}$, less than 0.001 $O.D._{600\ nm}$, less than 0.002 $O.D._{600\ nm}$, less than 0.003 $O.D._{600\ nm}$, less than 0.004 $O.D._{600\ nm}$, less than 0.005 $O.D._{600\ nm}$, less than 0.006 $O.D._{600\ nm}$, less than 0.007 $O.D._{600\ nm}$, less than 0.008 $O.D._{600\ nm}$, less than 0.009 $O.D._{600\ nm}$, less than 0.01 $O.D._{600\ nm}$, less than 0.02 $O.D._{600\ nm}$, less than 0.03 $O.D._{600\ nm}$, less than 0.04 $O.D._{600\ nm}$, less than 0.05 $O.D._{600\ nm}$, less than 0.06 $O.D._{600\ nm}$, less than 0.07 $O.D._{600\ nm}$, less than 0.08 $O.D._{600\ nm}$, less than 0.09 $O.D._{600\ nm}$, less than 0.1 $O.D._{600\ nm}$, less than 0.2 $O.D._{600\ nm}$, less than 0.3 $O.D._{600\ nm}$, less than 0.4 $O.D._{600\ nm}$, less than 0.5 $O.D._{600\ nm}$, less than 0.6 $O.D._{600\ nm}$, less than 0.7 $O.D._{600\ nm}$, less than 0.8 $O.D._{600\ nm}$, less than 0.9 $O.D._{600\ nm}$, less than 1.0 $O.D._{600\ nm}$, less than 1.5 $O.D._{600\ nm}$, or less than 2.0 $O.D._{600\ nm}$.

In some embodiments, yeast library-a and yeast library-α are cultured under dilute yeast cell conditions. For example, the yeast populations are grown separately in liquid yeast culture medium until the end of log phase. Various volumes of yeast libraries-a and cc can be mixed in flasks containing yeast culture medium and incubated at 30° C. without shaking. The yeast cells can then be counted and serial dilution can be performed to create a series of concentrations of yeast library cell mixtures to test for guided mating induced by the interaction of the receptor with their cognate cell surface ligand. Negative control mixtures can also be produced using serially diluted mixtures of yeast strains containing receptors and cell surface ligands that do not interact. The serially diluted yeast cell mixtures can be incubated, for any number of days, for example, for 1-7 days, to allow for diploid cells to form (FIG. 1). The diploid cells are then detected by incubating the cells in selective medium. The medium can contain, for example, both HYgR and KanMX. Diploid cells arising from the highest diluted mixtures, where no cells or very few cells, can be detected for the negative control samples, are selected for recombination. Mating factor can be induced in the haploid yeast cells at various concentrations. The yeast cell libraries can also contain sequences coding for mating factor, the expression of which, can be controlled by an inducible promoter, such as Gal1.

In some embodiments, the binding affinity between the first cell surface protein and the second cell surface protein is greater than the mating strain binding affinity between a yeast cell from the first mating strain and a yeast cell from the second mating strain. In certain embodiments, the binding affinity is at least two-fold, five-fold, ten-fold, twenty-five fold, fifty-fold, one hundred-fold, five-hundred fold, or one thousand-fold greater than the mating strain affinity. For example, the binding affinity can be at least two-fold, five-fold, ten-fold, twenty-five fold, fifty-fold, one hundred-fold, five-hundred fold, or one thousand-fold greater than the binding affinity between a-factor and the a-factor receptor and/or the binding affinity between the α-factor and the α-factor receptor.

After mating, the cultures can be maintained in selective liquid culture medium to allow selection of diploid cells. In some embodiments, the methods further comprising using at least one of the selectable markers to select for diploid cells that contain at least one each of the first and second plasmids after contacting the first plurality of haploid yeast cells with the second plurality of haploid yeast cells. The selective liquid culture medium can comprise antibiotics or other selective compound or lack specific nutrients. After selection, the viable diploid cells in the liquid medium may be streaked onto plates with solid selective medium for colony growth and replica plating.

In another embodiment, mating is performed by mixing liquid haploid yeast cell library cultures under dilute conditions, followed by streaking the mating mixtures on plates comprising solid medium. In an embodiment, serial dilutions of the liquid haploid yeast cells library cultures are performed prior and/or after mixing the cultures. The yeast cell culture concentration at the limiting dilution may also be determined by the spectral absorbance at $O.D._{600\ nm}$. The limiting dilution may have a spectral absorbance of less than 0.0001 $O.D._{600\ nm}$, less than 0.001 $O.D._{600\ nm}$, less than 0.002 $O.D._{600\ nm}$, less than 0.003 $O.D._{600\ nm}$, less than 0.004 $O.D._{600\ nm}$, less than 0.005 $O.D._{600\ nm}$, less than 0.006 $O.D._{600\ nm}$, less than 0.007 $O.D._{600\ nm}$, less than 0.008 $O.D._{600\ nm}$, less than 0.009 $O.D._{600\ nm}$, less than 0.01 $O.D._{600\ nm}$, less than 0.02 $O.D._{600\ nm}$, less than 0.03 $O.D._{600\ nm}$, less than 0.04 $O.D._{600\ nm}$, less than 0.05 $O.D._{600\ nm}$, less than 0.06 $O.D._{600\ nm}$, less than 0.07 $O.D._{600\ nm}$, less than 0.08 $O.D._{600\ nm}$, less than 0.09 $O.D._{600\ nm}$, less than 0.1 $O.D._{600\ nm}$, less than 0.2 $O.D._{600\ nm}$, less than 0.3 $O.D._{600\ nm}$, less than 0.4 $O.D._{600\ nm}$, less than 0.5 $O.D._{600\ nm}$, less than 0.6 $O.D._{600\ nm}$, less than 0.7 $O.D._{600\ nm}$, less than 0.8 $O.D._{600\ nm}$, less than 0.9 $O.D._{600\ nm}$, less than 1.0 $O.D._{600\ nm}$, less than 1.5 $O.D._{600\ nm}$, or less than 2.0 $O.D._{600\ nm}$. In certain embodiments, mating factor is induced prior to, after or at the time of mixing at a sufficient amount to promote preferential mating of haploid yeast cells that have undergone protein-protein interaction between the heterologous cell surface proteins. In some embodiments, the plates comprise select limited nutrients or selective medium for selection of diploid cells. In certain embodiments, the haploid yeast cells of one or both mating types harbor an auxotrophic requirement or genetic deficiency that is rescued upon diploid formation. In other embodiments, the haploid yeast cells harbor different selectable markers such as antibiotic resistance, and the antibiotics are incorporated into the selection medium.

In certain embodiments, mating is promoted by inducing the expression of a-factor and/or α-factor. In other embodiments the level of induction of the expression of a-factor and/or α-factor is titrated to a level that allows optimal mating of haploid yeast cells wherein the mating preferentially occurs between the haploid cells that have undergone protein-protein interactions of the cell surface proteins heterologously expressed on the opposite mating type haploid cells.

After mating and selection of viable diploid cells, colonies are grown on plates with solid medium. The colonies are then picked and inoculated onto separate containers with liquid culture or separate regions on plates with solid medium. In certain embodiments, the DNA from the colonies is isolated, optionally amplified and sequenced to identify the interacting heterologous proteins within the diploid cells. In certain embodiments, the sequences comprising a nucleic acid encoding a heterologous protein further comprise a sequence(s) that binds to oligonucleotide primers for performing polymerase chain reaction. In another aspect of the invention, the nucleic acid encoding a heterologous protein comprises a sequence that binds to an oligonucleotide adapter for high-throughput sequencing. In an exemplary embodiment of the invention, the adapters are double stranded DNA adapters that bind to the sequence. In an embodiment of the invention, the sequence encoding the cell surface protein is sequenced. In another embodiment of the invention, the molecular barcode sequence is sequenced. In certain embodiments, the sequencing is high-throughput sequencing.

Recombination and Sequencing

Figure 2:
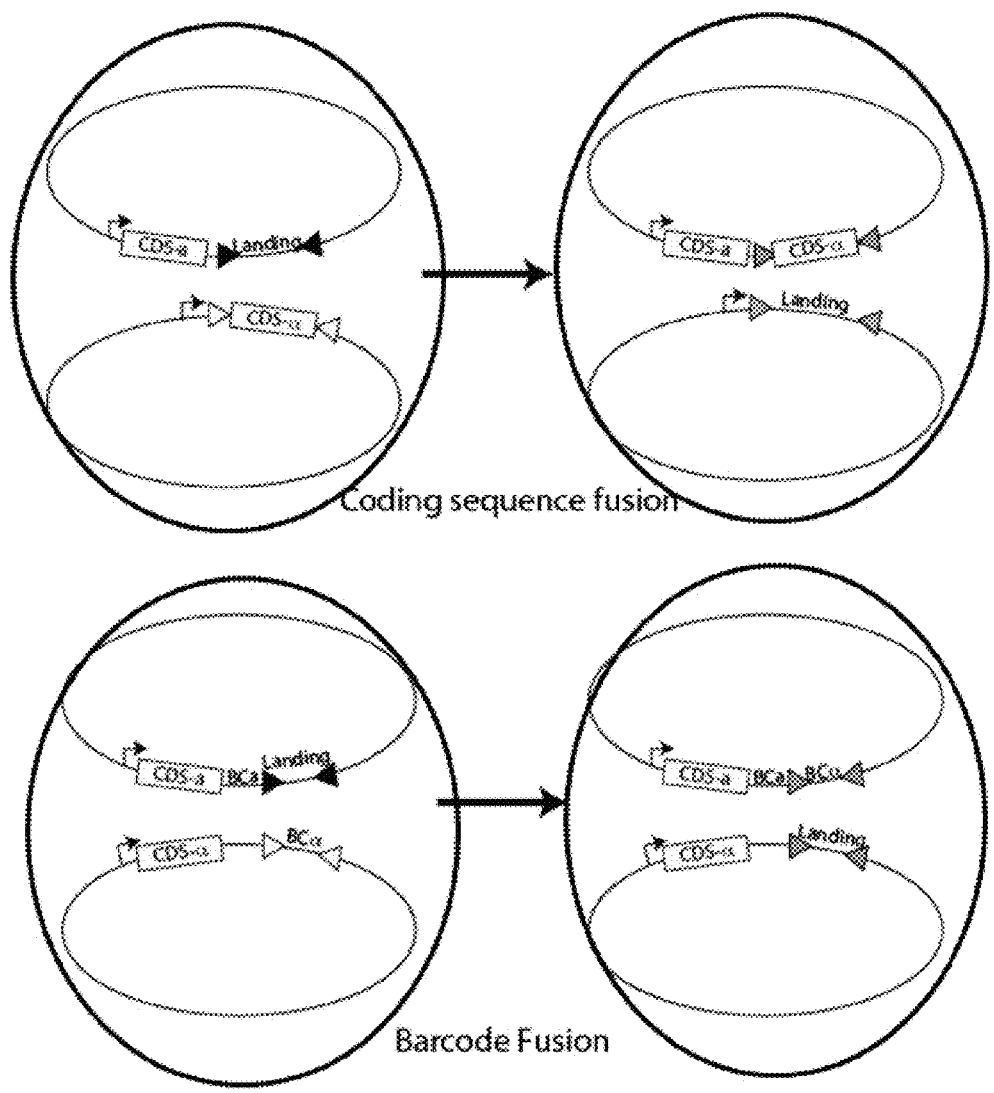
FIG. 2 is a schematic showing recombination of plasmids in diploid cells after guided mating of cell surface protein coding sequences. The top four plasmid diagrams depict recombination of the sequences (coding DNA sequence (CDS)) encoding the cell surface proteins in the diploid cell after mating. Recombination sites (triangles) flanking the CDS-a and CDS-a coding sequences are used to induce recombination of CDS onto a single plasmid. The bottom four plasmids depict recombination between barcode sequences (BC) in the diploid cell after mating. Recombination sites flanking the BCα recombines with two recombination sites downstream of BCα leading to a single plasmid with both barcode sequences.

The sequences encoding cell surface proteins from the library of first plasmids and the sequences encoding cell surface proteins from the library of second plasmids can be flanked by sequences that direct site-specific recombination, such as loxP sites that are used for directing CRE recombination (FIG. 2). In some embodiments, the yeast cells can also contain sequences that code for the expression of the CRE recombinase, operationally linked to an inducible promoter. For example, after mating and growth of the diploid cells, expression of CRE recombinase is induced and the recombination between the plasmids in the diploid cells leads to a recombined plasmid comprising the sequences that code for a cell surface protein from the library of first plasmids and a cell surface protein from the library of second plasmids. The sequences directing the recombination can be located on both the 3' and 5' end of one of the plasmids and only the 3' or 5' end of the second plasmid. The location of the sequences directing the recombination may be adjacent to the 3' or 5' ends or separated by any number of nucleotides that still confer efficient recombination. For example, as shown in FIG. 2 (upper) for coding sequence fusion, the filled-in triangles on the "a" plasmid is on the 3' end of the protein coding sequence ("CDS-a"). The protein coding sequence ("CDSα") on the second plasmid can be flanked by the sequences directing the recombination (empty triangles). After recombination has occurred, the corresponding fusion sequence can then be analyzed by sequencing, for example, by high throughput sequencing, such as Illumina® sequencing or other sequencing methods described herein.

As set forth above, in some embodiments, yeast plasmid libraries are constructed wherein unique oligonucleotide barcode sequences (BC) are associated with a unique cell surface protein in the library. In exemplary embodiments, the barcode sequences can be located at positions adjacent or separated by any number of nucleotides to the sequence coding for a receptor and cell surface ligand (FIG. 2, lower). For example, the plasmids may be constructed such that two LoxP sites flank the barcode sequence of the alpha type yeast cells and two LoxP sites are located downstream of the bar code sequence of the A type yeast cells. The two LoxP sites can be adjacent to the barcode sequences or any number of nucleotides separated and on either side of the barcode sequences. The yeast cells can also contain sequences that code for the expression of an enzyme or protein that directs recombination, such as CRE recombinase, operationally linked to an inducible promoter. For example, after mating and growth of the diploid cells, expression of CRE recombinase can be induced and recombination between the plasmids in the diploid cells produces a recombined plasmid comprising portions of the two barcode sequences from the alpha and A cells. The recombined sequences coding for at least a portion of each of the two barcode sequences can then be sequenced by high throughput sequencing, such as Illumina® sequencing, or other sequencing methods described herein.

Barcode fusion is useful in instances where fusion of the two coding sequences of the cell surface proteins involved in the protein-protein interaction exceeds the read-length of DNA sequencing platforms for unambiguous identification. Additionally, diploid yeast cells can be sorted based on a selectable marker that becomes active only in the diploid state (i.e., recombination of a promoter in a-type cells with a promoter-less fluorophore in the a-type cell). Diploid cells are then emulsified and/or lysed, and the barcodes and/or coding sequences for the cell surface proteins are sequenced by high throughput sequencing.

Importantly, the methods of this invention are not limited to assaying transmembrane protein interactions. For example, other proteins can be displayed on the cell surface and their interactions can also be captured using this approach. For example, at least a portion of a native soluble protein that is not normally associated with the plasma membrane or expressed on the cell surface can be engineered to be fused to at least a portion of a native cell surface protein in order to create a hybrid protein. For example, the soluble protein may be fused to at least a portion of a hydrophobic transmembrane domain of a native cell surface protein to create a hybrid protein. The soluble protein may also be fused to a linker polypeptide in between the soluble protein and the transmembrane domain. The linker polypeptide may be of any length of amino acids sufficient for membrane insertion of the transmembrane domain and correct folding and display of the of the soluble protein portion of the hybrid protein on the outer surface of the cell. The hybrid protein can also be engineered to contain a signal peptide sequence on the N-terminus of the polypeptide sequence for recognition by the endoplasmic-reticulum targeting machinery and entrance of the hybrid protein into the secretory pathway. The soluble protein may be fused to other hydrophobic domains which function to anchor the attached soluble protein to the plasma membrane. For example, the isolated N-terminal signal peptide and anchor domains of a natural type II integral membrane protein may be fused to a soluble protein. The expression of the hybrid protein in the haploid yeast cell can then lead to display of the portion of the native soluble protein on the outer surface of the haploid yeast cell, and thus, allow for identification of proteins that interact with the native soluble protein.

One of the advantages of this approach is that single libraries (i.e., libraries for the expression of, e.g., a few thousand proteins) are relatively easy to construct. Libraries designed to assay protein-protein interactions, are orders of magnitude more complex. For example, to test the pairwise interactions between 1000 proteins would require a library of size 1000*1000=1M. By simply creating two libraries and allowing them to interact, the library sizes become more manageable and modular.

Compositions

Provided herein are compositions comprising a first plurality of haploid yeast cells of a first mating type, the first plurality of cells comprising a library of first plasmids, wherein each plasmid in the library comprises a first selectable marker, a unique molecular barcode sequence operatively linked to a first recombination site, and a sequence encoding a unique cell surface protein, such that each unique molecular barcode is associated with a unique cell surface protein. The compositions can further comprise a second plurality of haploid yeast cells of a second mating type, the second plurality of cells comprising a library of second plasmids, wherein each plasmid in the library comprises a second selectable marker, a unique oligonucleotide molecular barcode sequence operatively linked to a second recombination site, and a sequence encoding a unique cell surface protein, such that each unique molecular barcode is associated with a unique cell surface protein, wherein the unique cell surface proteins of the library of first plasmids and the unique cell surface proteins of the library of second plasmids comprise potential specific binding pairs.

Also provided is a kit for the detection of protein-protein interactions of cell surface proteins expressed on haploid yeast cells comprising a plurality of plasmids, wherein each plasmid comprises: a selectable marker, a unique oligonucleotide molecular barcode sequence operatively linked to a recombination site, and a sequence encoding a cell surface protein, wherein each unique molecular barcode is associated with a unique cell surface protein. The kit can further comprise instructions for use. The compositions and kits may include any of the embodiments described herein.

Disclosed are materials, compositions, and components that can be used for, can be used in conjunction with, can be used in preparation for, or are products of the disclosed embodiments. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed, and a number of modifications that can be made to a number of molecules included in the method are discussed, each and every combination and permutation of the method, and the modifications that are possible, are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); Adams, D. E. Gottschling, C. A. Kaiser and T. Stearns. 1998. Methods in yeast genetics. Cold. Spring Harbor Laboratory Press, Cold Spring Harbor; *Remington's Pharmaceutical Sciences,* 18th Edition (Easton, Pa.: Mack Publishing Company, 1990); and Carey and Sundberg *Advanced Organic Chemistry* $3^{rd}$ Ed. (Plenum Press) Vols A and B(1992).

Example 1

The following example demonstrates exemplary methods of culturing haploid yeast cells, preparation of yeast cell libraries and mating *S. cerevisiae* under dilute conditions.

Cultures of haploid yeast cell libraries of a single mating type are serially maintained in YEPD medium comprising yeast extract, peptone and dextrose, at about 30° C. Preparation of the yeast cDNA libraries are performed by transforming the haploid yeast cells using a Lithium acetate protocol described by Gietz and Woods, et al. *Methods Enzymol.* 2002; 350:87-96).

Haploid cells are grown to mid-log phase ($OD_{610}$=1.6) prior to transformation. Washed, intact yeast cells are immediately mixed with PEG, LiAc, plasmid DNA and single-stranded carrier DNA and incubated at 42° C. for 40-60 min. The yeast strain is inoculated into 5 ml of liquid medium (2×YPAD or synthetic complete [SC] selection medium) and is incubated overnight at 30° C. The titer of the yeast culture is determined by measuring the $OD_{600}$ of a solution of 10 μl of the cells added to 1.0 ml of water in a spectrophotometer cuvette. 50 ml of pre-warmed 2×YPAD is transferred to the pre-warmed culture flask and $2.5 \times 10^8$ cells is added to give a density of $5 \times 10^6$ cells/ml. The flask is incubated on a rotary or reciprocating shaker at 30° C. and 200 rpm. When the cell titer is at least $2 \times 10^7$ cells/ml, the cells are harvested by centrifugation, washed in 25 ml of sterile water, and washed again in 1 ml of sterile water. Water is added to a final volume of 1.0 ml then mixed by vigorous vortexing to resuspend the cells. 100 μl samples (~$10^8$ cells) are pipetted into 1.5-ml microcentrifuge tubes, one for each transformation, centrifuge at top speed for 30 s, and the supernatant is discarded. 360 μl of transformation mix, consisting of 240 μl PEG 3350 [50% (w/v)], 36 μl LiAc (1.0 M), 50 μl boiled single-stranded DNA (2.0 mg/ml), and 34 μl plasmid DNA plus water is added to each transformation tube, and the cells are resuspend by vigorous vortex-mixing. The tubes are then incubated in a 42° C. water bath for 40 min. The tubes are then microcentrifuged at top speed for 30 s and the transformation mix is removed with a micropipette. 1.0 ml of sterile water is then pipetted into each tube, the pellet is stirred with a micropipette tip, and then vortexed. The appropriate dilutions of the cell suspension are then plated onto SC medium containing antibiotics used for selection, hygromycin B or KanMX.

The mating of the haploid yeast cell libraries is performed by growing the separate haploid yeast cell library cultures of opposite mating type to the end of log phase, then mixing the liquid haploid yeast cell library cultures under the dilute conditions, followed by streaking the mating mixtures on plates comprising solid medium. The two libraries of opposite mating type yeast cells are mixed and incubated at under dilute enough conditions that promote cell-cell contact only when there is specific binding between the two haploid cells. The yeast cell culture concentration under dilute conditions is between 0.001 $O.D._{600\ nm}$ and 0.1 $O.D._{600\ nm}$. After incubation, mating is triggered by induction of mating factor expression, and diploid cells are propagated by simultaneously selecting for the two selectable markers from the original haploid cells. The plates comprise solid medium and both hygromycin B and KanMX for selection of diploid cells harboring both selective markers. After mating and selection of viable diploid cells, individual colonies are grown on plates with solid selection medium and recombination is induced between the plasmids in the diploid cells. The colonies are then picked and inoculated onto separate containers with liquid culture. The DNA from the colonies is isolated, amplified and sequenced by high throughput Illumina® sequencing to identify the heterologous genes present within each of the diploid colonies.

Example 2

The following example demonstrates use of the invention to decode the T-cell receptor (TCR)/peptide-Maj or Histocompatibility Complex ligand (pMHC) relationship (TCR/pMHC). Two simplified plasmid cDNA libraries are constructed to be used as a positive control for the optimization of mating conditions. Each simplified plasmid cDNA library can comprise sequences coding for single transmembrane domain T-cell receptors or sequences coding for a cognate cell surface ligands for each receptor (pMHC). cDNA sequences derived from the human acute T cell leukemia cell line, Jurkat cells, encoding cell surface TCR proteins and cognate cell surface MHC ligand proteins are cloned using standard molecular biology techniques into separate plasmids. The TCR sequences are derived from public databases as well as in-house sequencing data. The sequences of the pMHC library members are derived from in silico prediction of peptides derived from genes of interest. In addition, cDNA libraries derived from Jurkat cells are also commercially available (GeneCopoeia). The cDNA sequences from the Jurkat cell plasmid libraries are cloned into library expression vectors harboring selectable markers and loxP recombination sites. The cloned sequences are linked to a promoter sequence (viral promoter CMV5) to drive expression of the TCR and MHC ligands as well as a selectable marker.

The plasmid libraries are used to transform competent yeast cells (Saccharomyces cerevisiae), as described in Example 1 above, to create yeast cell libraries comprising the plasmids. For profiling protein-protein interactions of T-cell receptor (TCR)/peptide and Major Histocompatibility Complex ligands (pMHC), yeast cell libraries are constructed by transforming haploid yeast cells of opposite mating type with the cDNA libraries derived from Jurkat cells. The yeast cell libraries are made using resistance to the antibiotic, hygromycin B or KanMX. The plasmid library encoding the receptors are transformed into mating type A haploid yeast cells (yeast library-a) wherein the a-type haploid yeast cells harbor hygromycin B resistance, and the plasmid library encoding the cognate cell surface ligands (yeast library) are transformed into mating type alpha haploid yeast cells harboring KanMX resistance. Alternatively, the selectable marker (HYgR) is encoded in the plasmids carrying the sequence encoding the receptors and the selectable marker (KanMX resistance) is encoded in the plasmids carrying the sequence for the cell surface ligand. The yeast cell libraries are each grown and maintained on selective medium harboring either HYgR or KanMX, respectively.

Yeast library-a and yeast library-a are cultured and mated under dilute yeast cell conditions, as described in Example 1 above. In order to determine optimal dilute concentrations of yeast cells for mating, serial dilutions are performed and tested for diploid formation and resulting numbers of diploid formation and guided mating by protein-protein interactions of the heterologous TCR and cognate pMHC. Various volumes of the yeast libraries-a and a are mixed in flasks containing yeast culture medium and incubated at 30° C. without shaking. The yeast cells are counted and serial dilution is performed to create a series of concentrations of yeast library cell mixtures to test for guided mating induced by the interaction of the TCR with their cognate pMHC. Negative control mixtures are also produced using serially diluted mixtures of yeast strains containing receptors containing individual receptors and cell surface ligands that do not interact. The yeast cell libraries also contain sequences coding for mating factor, the expression of which, is controlled by the inducible promoter, Gal1. Mating factor is induced in the haploid yeast cells at various concentrations to test for the optimal expression of mating factor for selective mating of pairs that have undergone TCR/pMHC interaction.

The serially diluted yeast cell mixtures are incubated for 1-7 days to allow for diploid cells to form (FIG. 1). The diploid cells are then detected by incubating the cells in selective medium containing both HYgR and KanMX. Diploid cells arising from the highest diluted mixtures, where no cells or very few cells can be detected for the negative control samples, are selected for recombination.

The sequences encoding the receptor and cell surface ligands are flanked by loxP sites that are used for CRE recombination (FIG. 2). The yeast cells also contain sequences that code for the expression of the CRE recombinase, operationally linked to an inducible promoter (such as Tet-ON system where CRE is induced by addition of Doxycyclin). After mating and growth of the diploid cells, expression of CRE recombinase is induced and the recombination between the plasmids in the diploid cells leads to a recombined plasmid comprising the sequences that code for both the TCR and the pMHC.

The recombined sequences coding for the receptor and cell surface ligand are then sequenced by Illumina® sequencing. DNA is isolated from the diploid library, and primers complementary to sequences flanking the recombined coding sequences are used to amplify at least a portion of the pair-wise recombined coding sequences within the extracted DNA from the diploid library. A high-throughput sequencing library is prepared from the amplified library and sequenced by Illumina® sequencing.

Example 3

This following example demonstrates use of an embodiment of the invention to identify (TCR/pMHC) by sequencing recombined barcode sequences. Unique oligonucleotide barcode sequences 20 nucleotides in length are generated for each cDNA sequence in the Jurkat cDNA expression libraries generated as described in Example 1 above. The barcode sequences are produced using barcoded oligonucleotide adapters during the reverse transcription of mRNAs to generate the barcoded cDNAs that are cloned into the library plasmid (Hafner et al., 2013).

Plasmid cDNA libraries of opposite mating type comprising TCR sequences pMHC sequences as described in Example 2. Barcode sequences are engineered to be located at positions adjacent to the sequence coding for the TCR and pMHC using standard molecular biology techniques (FIG. 2). Two LoxP sites flank the barcode sequence of the alpha type yeast cells of the alpha type yeast cell libraries and two LoxP sites are located downstream of the bar code sequence of the A type yeast cells of the A type yeast cell libraries. The yeast cells also contain sequences that code for the expression of the CRE recombinase, operationally linked to an inducible promoter (such as, Tet-ON, induced by doxycyclin). After mating under dilute conditions, selection and growth of the diploid cells as described in Example 1, the expression of CRE recombinase is induced and the recombination between the plasmids in the diploid cells leads to a recombined plasmid comprising portions of the two barcode sequences from the alpha and A cells.

Following recombination to generate the recombined barcode sequence, DNA is isolated from the diploid library, and constant primers flanking the recombined barcode sequence are used to amplify all of the pair-wise recombined barcodes within the extracted DNA from the diploid library. A high-throughput sequencing library is prepared from the amplified barcode library and sequenced by Illumina® sequencing. Sequence analysis of the resulting sequences reveals the pair-wise specificity of the original TCR and pMHC sequences.

While the invention has been particularly shown and described with reference to a preferred embodiment and various alternate embodiments, it will be understood by persons skilled in the relevant art that various changes in form and details can be made therein without departing from the spirit and scope of the invention.

What is claimed is:

1. A method of detecting a protein-protein interaction between cell surface proteins, the method comprising:
   (a) providing a first plurality of haploid yeast cells of a first mating type, the first plurality of cells comprising a library of first plasmids, wherein each plasmid in the library comprises:
      a first selectable marker, a first unique oligonucleotide molecular barcode sequence operatively linked to a first recombination site, and a sequence encoding a unique cell surface protein, such that each unique molecular barcode is associated with a unique cell surface protein;
   (b) providing a second plurality of haploid yeast cells of a second mating type, the second plurality of cells comprising a library of second plasmids, wherein each plasmid in the library comprises:
      a second selectable marker, a second unique oligonucleotide molecular barcode sequence operatively linked to a second recombination site, and a sequence encoding a unique cell surface protein, such that each unique molecular barcode is associated with a unique cell surface protein,
      wherein the unique cell surface proteins of the library of first plasmids and the unique cell surface proteins of the library of second plasmids comprise potential binding pairs;
   (c) contacting the first plurality of haploid yeast cells with the second plurality of haploid yeast cells under dilute yeast cell conditions that promote contact between the first plurality of haploid yeast cells and the second plurality of haploid yeast cells when a specific binding interaction between a cell surface protein of the library of first plasmids and a cell surface protein of the library of second plasmids occurs, wherein the specific binding interaction promotes mating of the first and second plurality of haploid yeast cells to produce diploid yeast cells;
   (d) recombining within the diploid cells portions of the plasmids to generate a recombined molecular barcode sequence comprising at least a portion of the unique barcode associated with one of the unique cell surface proteins of the library of first plasmids and a portion of the unique molecular barcode associated with one of the unique cell surface proteins of the library of second plasmids; and
   (e) sequencing at least a portion of the recombined molecular barcode sequence from the diploid cells to identify a surface protein from the library of first plasmids and a cell surface protein from the library of second plasmids that interact, thus detecting a protein-protein interaction between the cell surface proteins.

2. The method of claim 1, further comprising using at least one of the selectable markers to select for diploid cells that contain at least one each of the first and second plasmids after contacting the first plurality of haploid yeast cells with the second plurality of haploid yeast cells.

3. The method of claim 1, wherein the recombined molecular barcode sequence from two or more diploid cells are sequenced to detect two or more different cell surface protein-protein interactions.

4. The method of claim 1, wherein the specific binding interaction between the first plurality of haploid yeast cells and the second plurality of haploid yeast cells occurs in a dilute mixture that has a spectral absorbance of less than 2.0 $O.D._{600\ nm}$.

5. The method of claim 1, wherein the binding affinity between the first cell surface protein and the second cell surface protein is greater than the mating type binding affinity between a yeast cell from the first mating type and a yeast cell from the second mating type.

6. The method of claim 5, wherein the binding affinity is at least two-fold, five-fold or ten-fold greater than the mating type affinity.

7. The method of claim 1, wherein the first selectable marker and the second selectable marker are the same.

8. The method of claim 1, wherein the first selectable marker and the second selectable marker are different.

9. The method of claim 1, wherein the recombination is site-specific recombination.

10. The method of claim 1, wherein the recombination is CRE-Lox recombination.

11. The method of claim 1, wherein the recombination is FLP-FRT recombination.

12. The method of claim 1, wherein the recombination is unidirectional integration.

13. The method of claim 12, wherein the recombination is catalyzed by a serine integrase.

14. The method of claim 13, wherein the recombination is catalyzed by a PhiC31 integrase.

15. The method of claim 1, wherein the first and the second unique oligonucleotide molecular barcode sequence is between 5 and 50 nucleotides in length.

16. The method of claim 1, wherein the plasmids recombine with the genome of the haploid yeast cell or the diploid yeast cell.

17. The method of claim 1, wherein the cell surface protein is a transmembrane protein.

18. The method of claim 1, wherein the cell surface protein is an integral membrane protein.

19. The method of claim 1, wherein the cell surface protein is peripheral membrane protein.

20. The method of claim 1, wherein the cell surface protein is encoded by a mammalian gene.

21. The method of claim 1, wherein the cell surface protein is encoded by a human gene.

22. The method of claim 1, wherein at least one of the haploid yeast cells have a gene coding for a yeast mating factor that is controlled by an inducible promoter.

23. The method of claim 22, wherein the inducible promoter is Gal1.

24. The method of claim 22, wherein the mating of the haploid yeast cells is induced by activating the inducible promoter.

25. The method of claim 1, wherein mating of the haploid yeast cells is detected by a marker that becomes active only in the diploid cells.

26. The method of claim 1, wherein the diploid cells are detected after recombination between the plasmids.

27. The method of claim 1, wherein the diploid cells are detected by the presence of two distinct selectable markers.

28. The method of claim 1, wherein sequencing comprises amplification of the recombined molecular bar code sequence.

29. The method of claim 1, wherein sequencing comprises amplification of at least a portion of the sequence that encodes the cell surface protein in a first plasmid or at least a portion of the sequence that encodes the cell surface protein in a second plasmid.

30. The method of claim 1, wherein the cell surface protein is a protein not normally associated with the cell membrane or expressed on the cell surface.

31. The method of claim 30, wherein the cell surface protein is a hybrid protein comprising at least a portion of a native, soluble protein fused to at least a portion of a native cell surface protein, wherein the at least a portion of the native, soluble protein is expressed on the outer surface of the haploid yeast cell.

32. The method of claim 31, wherein a linker connects the at least a portion of the native, soluble protein to the at least a portion of the native cell surface protein.

* * * * *